US008152712B2

(12) United States Patent
Abe

(10) Patent No.: US 8,152,712 B2
(45) Date of Patent: Apr. 10, 2012

(54) ENDOSCOPE SYSTEM AND METHOD FOR INSPECTING ELECTRONIC ENDOSCOPE

(75) Inventor: Kazunori Abe, Saitama (JP)

(73) Assignee: Fujifilm Corporation, Tokyo (JP)

( * ) Notice: Subject to any disclaimer, the term of this patent is extended or adjusted under 35 U.S.C. 154(b) by 386 days.

(21) Appl. No.: 12/401,338

(22) Filed: Mar. 10, 2009

(65) Prior Publication Data

US 2009/0234183 A1    Sep. 17, 2009

(30) Foreign Application Priority Data

Mar. 11, 2008    (JP) ................... 2008-060427

(51) Int. Cl.
*A61B 1/06* (2006.01)
*A61B 1/04* (2006.01)
(52) U.S. Cl. ......... 600/103; 600/101; 600/127; 600/118
(58) Field of Classification Search .................. 600/103, 600/109, 133, 160, 101, 169, 127; 348/71, 348/74, 17; 385/117, 116; 362/335, 574
See application file for complete search history.

(56) References Cited

U.S. PATENT DOCUMENTS

| | | | | |
|---|---|---|---|---|
| 4,980,763 | A * | 12/1990 | Lia ................... | 348/67 |
| 5,612,780 | A * | 3/1997 | Rickenbach et al. ........ | 356/73.1 |
| 5,868,666 | A * | 2/1999 | Okada et al. ................ | 600/118 |
| 6,388,742 | B1 * | 5/2002 | Duckett ................... | 356/73.1 |
| 6,452,624 | B1 * | 9/2002 | Aloy ................... | 348/71 |
| 6,885,801 | B1 * | 4/2005 | Shankar et al. ............ | 385/117 |
| 2005/0049457 | A1 * | 3/2005 | Leiner et al. ............... | 600/117 |
| 2007/0088193 | A1 * | 4/2007 | Omori et al. ............... | 600/101 |
| 2007/0147033 | A1 * | 6/2007 | Ogawa et al. .............. | 362/230 |
| 2008/0161646 | A1 * | 7/2008 | Gomez ................... | 600/169 |
| 2008/0228031 | A1 * | 9/2008 | Leiner et al. ............... | 600/109 |
| 2009/0073261 | A1 * | 3/2009 | Takemura et al. ........... | 348/71 |

FOREIGN PATENT DOCUMENTS

| | | |
|---|---|---|
| JP | 2002-058640 A | 2/2002 |
| JP | 2006-055664 A | 3/2006 |

* cited by examiner

*Primary Examiner* — John P Leubecker
*Assistant Examiner* — Ronald D Colque
(74) *Attorney, Agent, or Firm* — Birch, Stewart, Kolasch & Birch, LLP

(57) ABSTRACT

An electronic endoscope has a light guide for leading a light and a solid-state image sensor for capturing an image of a human body cavity during illumination. In inspecting the number of broken optical fibers in the light guide, a cap is attached to a distal portion of the electronic endoscope. The cap has a test chart. The solid-state image sensor captures an image of the test chart which is illuminated with the light transmitted through the light guide. A photometric circuit calculates an average luminance value "Y" of the test chart from a chart image signal. A broken fiber number calculator calculates the number "N" of broken optical fibers that satisfies $N = M \times (1 - Y/I)$. "Y" represents an average luminance value of the test chart. "I" represents an ideal average luminance value when all optical fibers are conducting, and "M" represents the total number of the optical fibers.

12 Claims, 8 Drawing Sheets

ENDOSCOPE SYSTEM AND METHOD FOR INSPECTING ELECTRONIC ENDOSCOPE

BACKGROUND OF THE INVENTION

1. Field of the Invention

The present invention relates to an endoscope system that is constituted of an electronic endoscope, a processor device and a light source device, and a method for inspecting the electronic endoscope.

2. Description Related to the Prior Art

An endoscope system is constituted of an electronic endoscope, a processor device and a light source device. The electronic endoscope has a solid-state image sensor at its distal portion for capturing an image of a human body cavity to output an image signal. The processor device receives the image signal from the solid-state image sensor and produces an image to display it on a monitor. The light source device supplies the electronic endoscope with light. Inside the electronic endoscope, a light guide extends. The light from the light source device is led into the distal portion of the electronic endoscope through the light guide, and is incident on the human body cavity from lighting windows provided in the distal portion.

The light guide consists of a plurality of optical fibers tied in a bundle and a binder such as a tape for wrapping the bundle. Since the optical fibers become rigid with a lapse of time, the optical fibers gradually deteriorate and finally snap due to stress applied in using the electronic endoscope. Accordingly, JPA No. 2006-55664 discloses to cover the optical fibers with a flexible tube which has holes formed at regular intervals, for the purpose of preventing a break of the optical fibers. Such a flexible tube, however, cannot always prevent the break because the optical fibers necessarily deteriorate with time.

The break of the optical fibers in the light guide causes reduction in the amount of light exiting from the light guide in accordance with the number of broken optical fibers. Thus, JPA No. 2002-58640 discloses to provide an aperture stop between an incident end of the light guide and a light source in order to keep the amount of exit light constant. The amount of light exiting from the light guide is measured based on an image signal from the solid-state image sensor. The aperture stop is actuated on the basis of a measurement result to control the amount of exit light. Adjustment by the aperture stop, however, is insufficient in a case where a predetermined number or more of optical fibers have already snapped. In this case, a shortage of light exiting from the light guide darkens the image, so that the light guide needs repairing.

A conventional endoscope system cannot detect the break of the optical fibers in the light guide. Therefore, a user cannot grasp appropriate timing of repairing the light guide, and hence it may happen that a doctor has found a shortage of exit light after inserting the electronic endoscope into a patient's body, and the electronic endoscope has to be pulled out and replaced. To prevent such an event, it is conceivable to repair the light guide early on before the electronic endoscope is short of the exit light. However, repair at an early stage causes increase in costs.

SUMMARY OF THE INVENTION

An object of the present invention is to provide an electronic endoscope inspection method that detects the number of broken optical fibers in a light guide, and to provide an endoscope system that correctly notifies a user of repair timing of the light guide on the basis of an inspection result.

An endoscope system is constituted of a cap having a test chart, a photometric circuit and a broken fiber number calculator. The cap is attached to a distal portion of an electronic endoscope so that a solid-state image sensor captures an image of the test chart. The photometric circuit measures an average luminance value of the test chart from an image signal of the test chart. The broken fiber number calculator calculates the number "N" of broken optical fibers that satisfies the following expression:

$$N = M \times (1 - Y/I)$$

wherein, "Y" represents the average luminance value detected by the photometric circuit. "I" represents an ideal average luminance value when all optical fibers are conducting, and "M" represents the total number of the optical fibers.

In the endoscope system, the processor device may contain the photometric circuit and the broken fiber number calculator.

In that case, the processor device may further comprise a first notification section for notifying a user of the number of the broken optical fibers.

The processor device may further comprise a second notification section for issuing a warning message, when the number of the broken optical fibers reaches or exceeds a predetermined number.

The processor device may further comprise an operation unit, a count detector and a third notification section. The operation unit causes the endoscope system to set a light guide inspection mode. The number of the broken optical fibers is calculated in the light guide inspection mode. The count detector detects the number of times the electronic endoscope has been used. The third notification section issues a message that reminds a user of inspection of the light guide, when the number detected by the count detector coincides with a predetermined number.

The processor device may further comprise an amplifier for amplifying the image signal and a gain adjuster for adjusting gain of the amplifier to correct decrease in the average luminance value with respect to the ideal average luminance value.

In the endoscope system, the test chart is preferably provided with a distance-measuring area. The processing unit further comprises a distance-measuring circuit for detecting distance from the distal portion to the test chart on the basis of the size of the distance-measuring area obtained from the image signal. The ideal average luminance value is corrected based on the distance detected by the distance-measuring circuit.

The distance-measuring area may be a circular black area.

The test chart may have a photometric area of 18% gray, and the photometric circuit calculates the average luminance value of the test chart from luminance of the photometric area obtained from the image signal.

In the endoscope system, the light source device may comprise a light source, an aperture stop mechanism, a timer, a memory and an aperture stop controller. The light source emits the light. The aperture stop mechanism is disposed between the light source and the light guide, and leads the light into the light guide. The timer counts used time of the light source. The memory stores light source property data which indicates the relation between a light emission amount and the used time of the light source. The aperture stop controller retrieves a light damping rate in the light emission amount from the used time and the light source property data, and controls opening of the aperture stop mechanism so that the amount of light led into the light guide is made constant irrespective of the light damping rate.

When the light damping rate is larger than a predetermined value and the amount of light led into the light guide is less than a predetermined value though the aperture stop mechanism is open to its maximum, the ideal average luminance value is corrected based on the light damping rate.

A method for inspecting an electronic endoscope comprises the steps of attaching a cap with a test chart to a distal portion of an electronic endoscope, illuminating the test chart with light which is emitted from a light source and transmitted through a light guide, capturing an image of the test chart by a solid-state image sensor, detecting an average luminance value of light obtained from an image signal outputted from the solid-state image sensor, and calculating the number "N" of broken optical fibers that satisfies the following expression:

$$N = M \times (1 - Y/I)$$

Wherein, "Y" represents the detected average luminance value. "I" represents an ideal average luminance value when all optical fibers are conducting, and "M" represents the total number of the optical fibers.

The endoscope system according to the present invention can correctly detect the number of broken optical fibers in the light guide. Therefore, the user can grasp appropriate timing of replacing the electronic endoscope and hence effectively use the electronic endoscope.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

Figure 1:
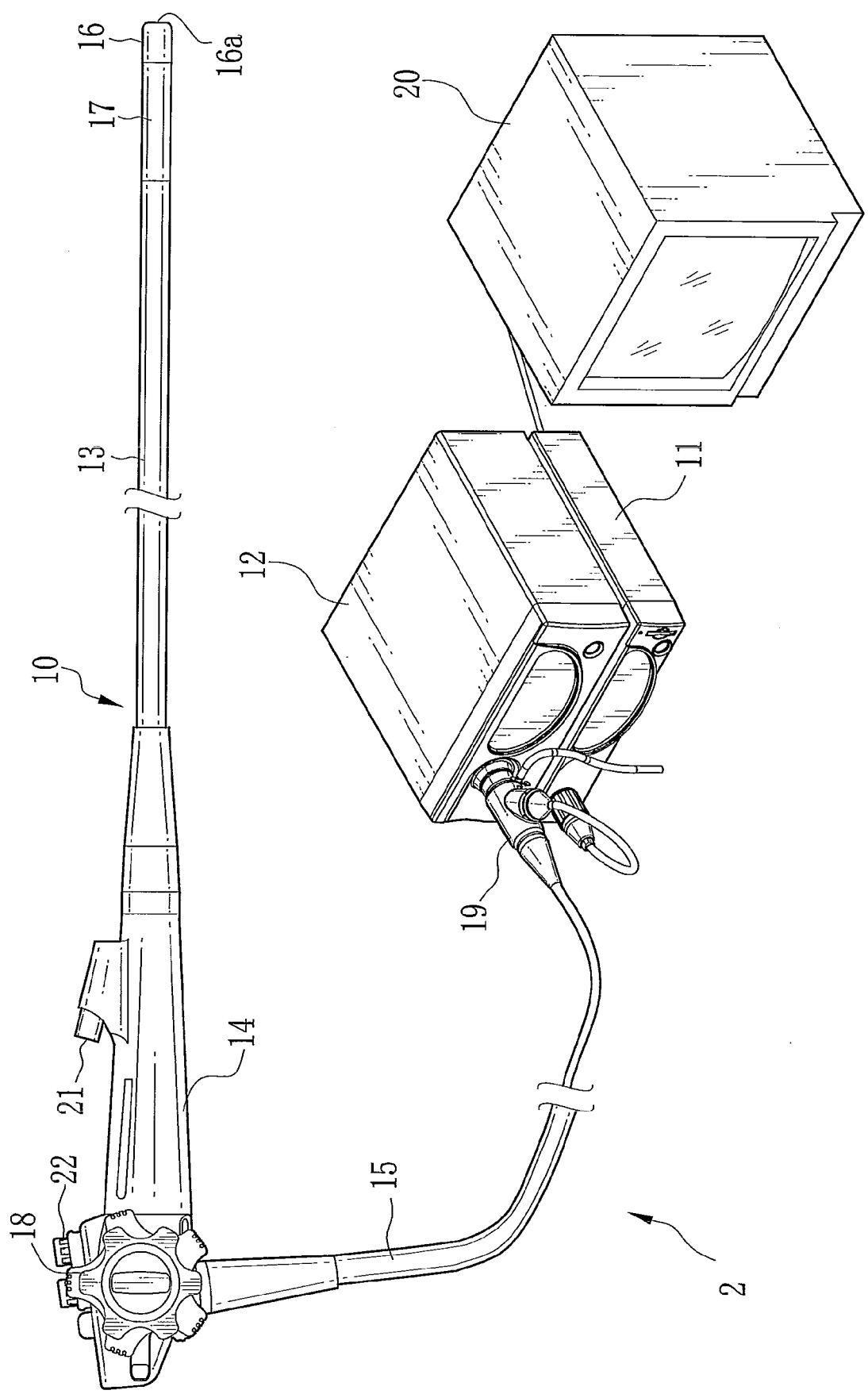
FIG. 1 is a schematic perspective view of an endoscope system.
Figure 3:
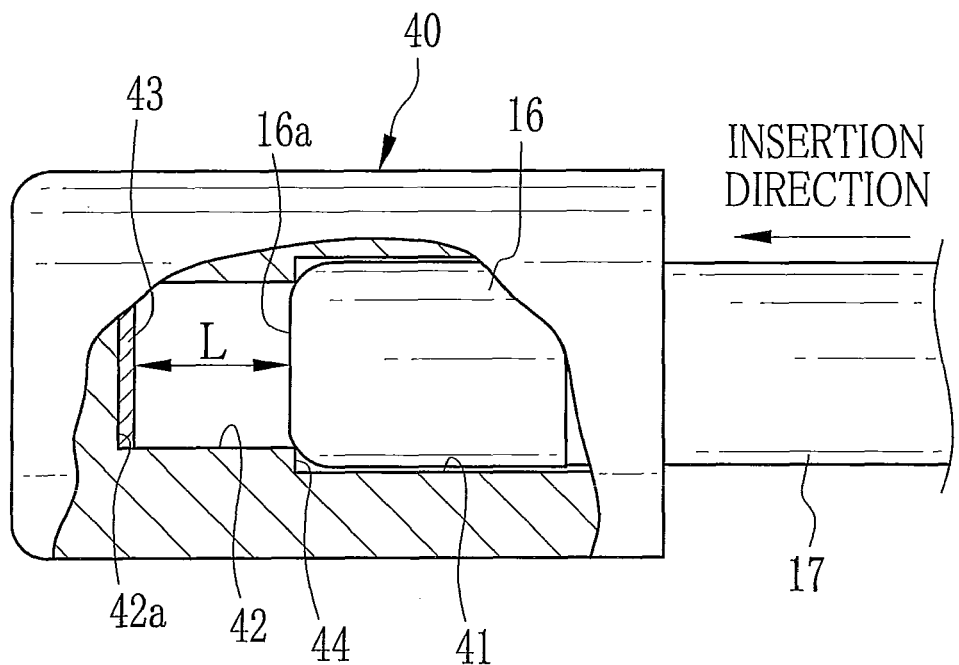
FIG. 3 is a partly broken sectional view for explaining the structure of a cap.

In FIG. 1, an endoscope system 2 consists of an electronic endoscope 10, a processor device 11, a light source device 12 and a cap 40 (see FIG. 3). The electronic endoscope 10 is provided with a flexible insert section 13 that is introduced into a human body cavity, an operation section 14 that is joined to a base end of the insert section 13, and a universal cord 15 that is connected to the processor 11 and the light source device 12.

At an end of the insert section 13 is provided a distal portion 16 that contains a solid-state image sensor (CCD) 50 for capturing an optical image of a target body part to inspect. Behind the distal portion 16, a bending portion 17 consisting of a number of linked ring-like segments is provided. By operating an angle knob 18 on the operation section 14, a number of wires extending in the insert section 13 are pulled and pushed to bend the bending portion 17 from side to side and up and down. Thus, the distal portion 16 is directed to the target body part inside the human body cavity.

To an end of the universal cord 15, a multi-connector 19 is attached. The connector 19 is detachably connected not only to the processor device 11 but also to the light source device 12. The processor device 11 is electrically connected to the light source device 12 via the connector 19, and has control over the endoscope system 2.

The processor device 11 feeds power to the electronic endoscope 10 through a transmission cable extending in the universal cord 15, and controls the actuation of the solid-state image sensor 50. The processor device 11 receives an image signal outputted from the solid-state image sensor 50, and subjects the image signal to various kinds of signal processing to produce image data. An image produced from the image data is displayed on a monitor 20, which is connected to the processor device 11 with a cable, as an endoscope image.

Figure 2:
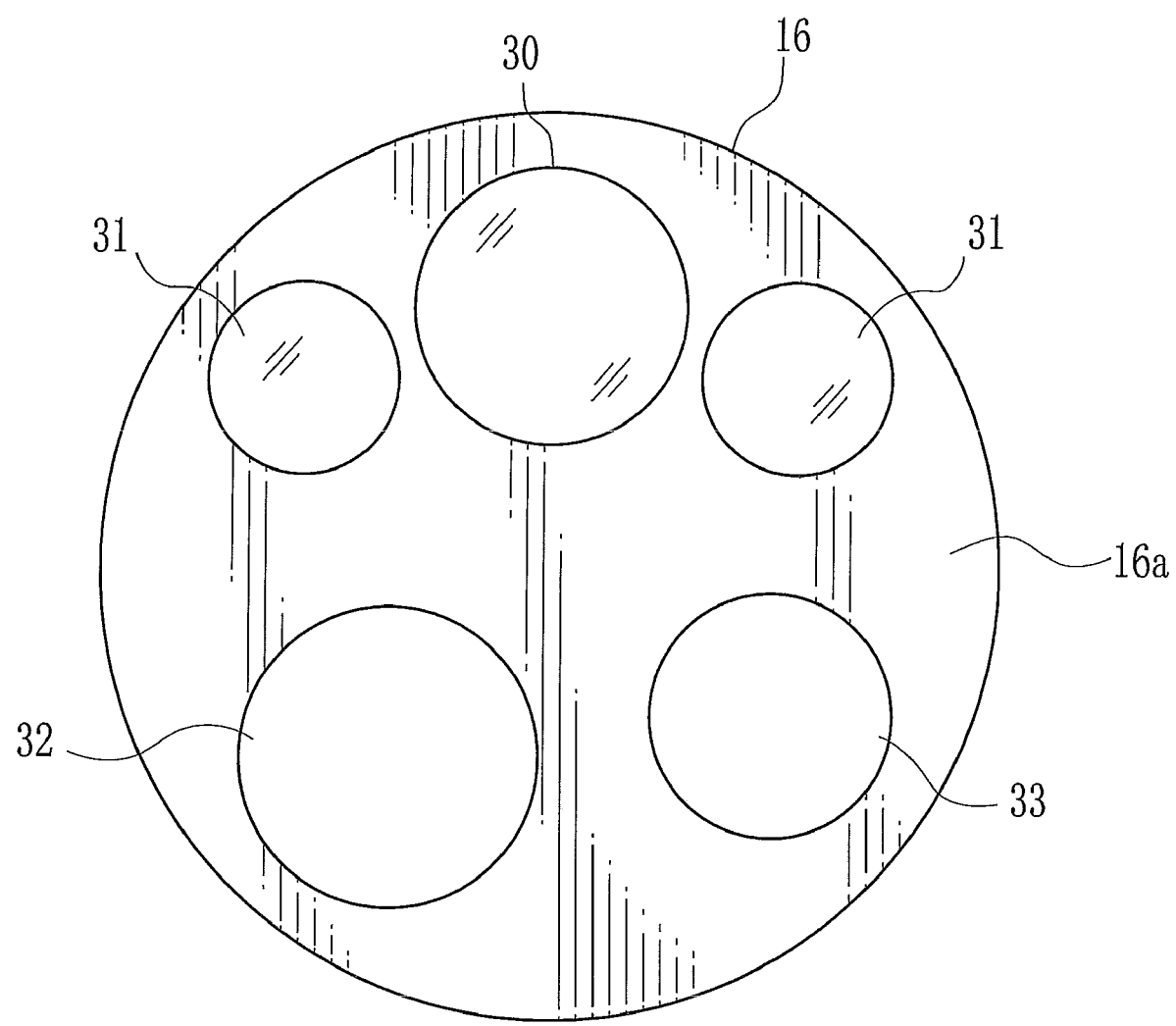
FIG. 2 is a front view of a distal portion of an electronic endoscope.

As shown in FIG. 2, a front face 16a of the distal portion 16 is provided with an image capturing window 30, lighting windows 31, a medical instrument outlet 32 and an air/water nozzle 33. The image capturing window 30 is disposed in the upper middle of the front face 16a. Behind the image capturing window, the solid-state image sensor 50 is disposed through an objective lens system 53 and a prism 54 (refer to FIG. 6).

The two lighting windows 31 symmetric with respect to the image capturing window 30 projects light that is guided from the light source device 12 through a light guide 80 and a lens 83 (refer to FIG. 6) to the target body part. The medical instrument outlet 32 is connected to a medical instrument insertion port 21 (refer to FIG. 1) on the operation section 14 through a channel extending in the insert section 13. A medical instrument with a forceps, a needle, a diathermy knife or the like at its tip is inserted into the medical instrument insertion port 21 in order to protrude the tip of the instrument from the medical instrument outlet 32 to the target body part.

The watering/airing nozzle 33 ejects water or air from an air/water reservoir contained in the light source device 12 to the image capturing window 30 or the target body part in response to actuation of a watering/airing button 21 (refer to FIG. 1) on the operation section 14.

The endoscope system 2 has a light guide inspection mode for inspecting the light guide 80. In this mode, as shown in FIG. 3, the cap 40 for tightly sealing the front face 16a is attached to the distal portion 16 of the electronic endoscope 10. The cap 40 is in the shape of a cylinder with a bottom. The cap 40 includes an insertion slot 41 that has the approximately same diameter as the distal portion 16, a light-shielding hole 42 continuous from the insertion slot 41, and a test chart 43 fitted into a bottom face 42a of the light-shielding hole 42. The diameter of the light-shielding hole 42 is smaller than that of the insertion slot 41. When the distal portion 16 of the electronic endoscope 10 is inserted into the insertion slot 41, the rim of the front face 16a comes into contact with a step 44 between the insertion slot 41 and the light-shielding hole 42, and the front face 16a faces to the test chart 43. The light illuminates the test chart 43 through the lighting windows 31. The solid-state image sensor 50 captures an image of the illuminated test chart 43 through the image capturing window 30.

Figure 4:
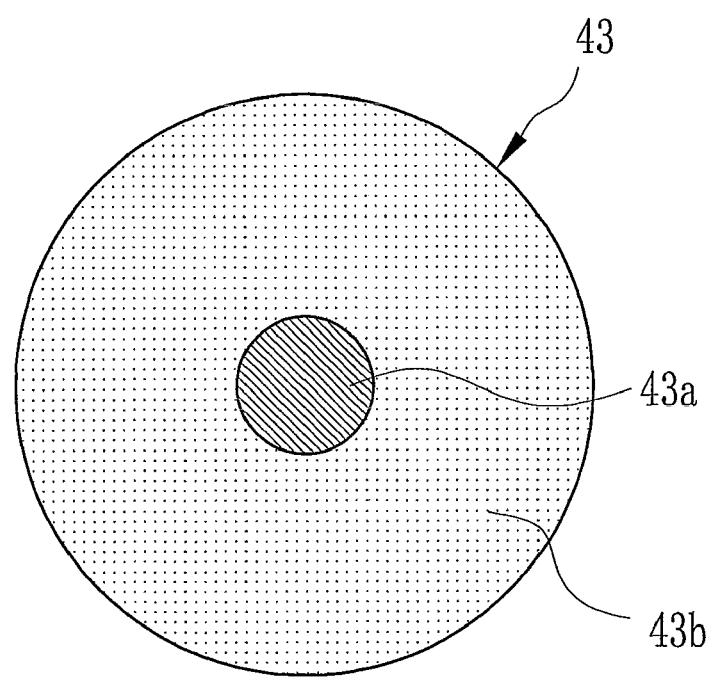
FIG. 4 is a plan view of a test chart.

The test chart 43, as shown in FIG. 4, has a distance-measuring area 43a and a photometric area 43b. The distance-measuring area 43a is a circular black area disposed in the center of the test chart 43. The distance-measuring area 43a is used for measuring a distance L (see FIG. 3) from the test chart 43 to the front face 16a of the distal portion 16. The photometric area 43b is an 18% gray area (gray of 18% reflectivity) disposed on the periphery of the distance-measuring area 43a. The photometric area 43b is used for white balance correction, in addition to the inspection of the light guide 80.

Figure 5:
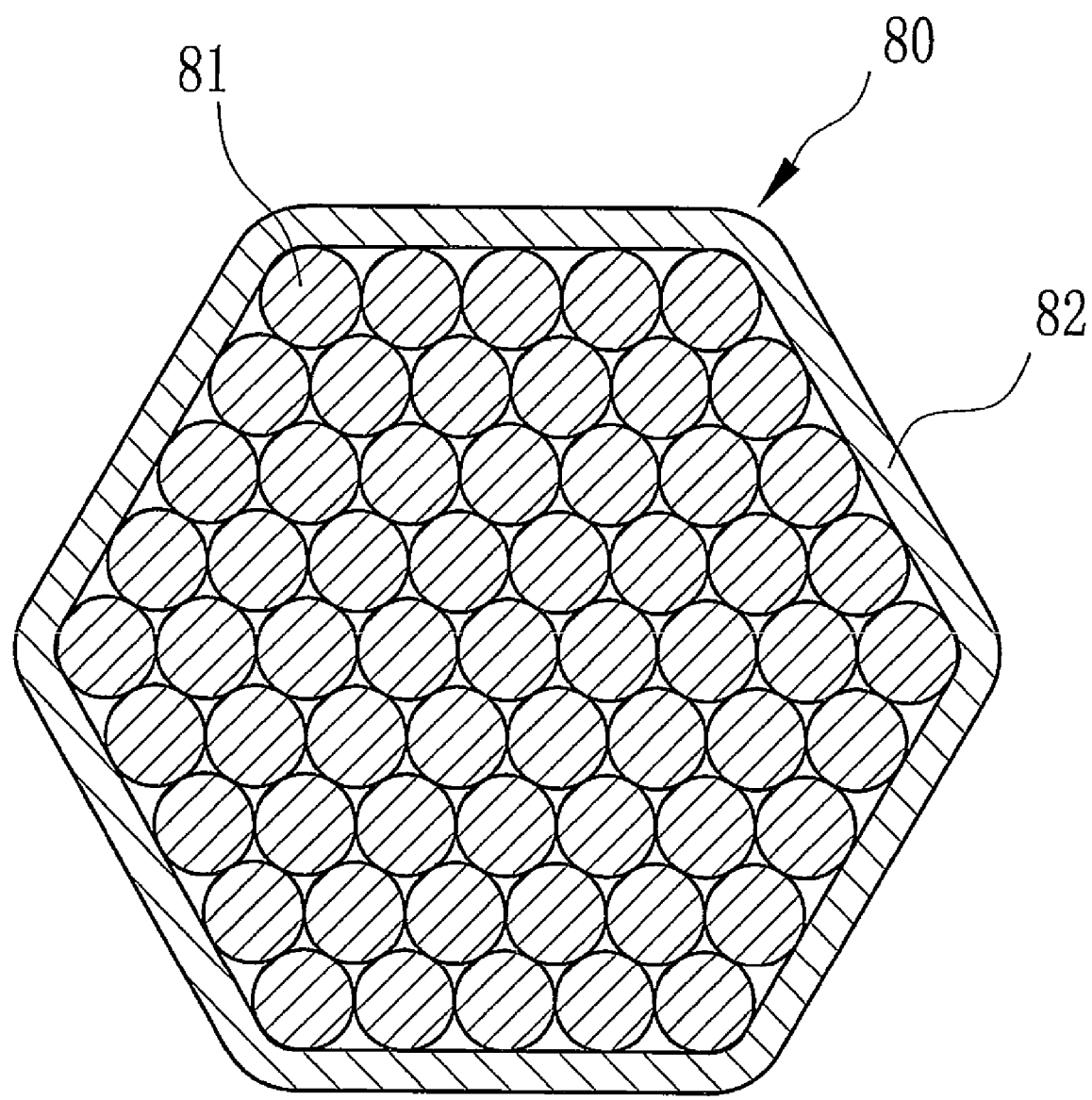
FIG. 5 is a cross-sectional view of a light guide.

As shown in FIG. 5, the light guide 80 consists of a bundle of many optical fibers 81 whose periphery is covered with a binder 82 such as a tape. Although all the optical fibers 81 are tied into a single bundle on a light incident side of the light guide 80, the bundle is branched off in two and led to the two lighting windows 31 on a light exit side.

Figure 6:
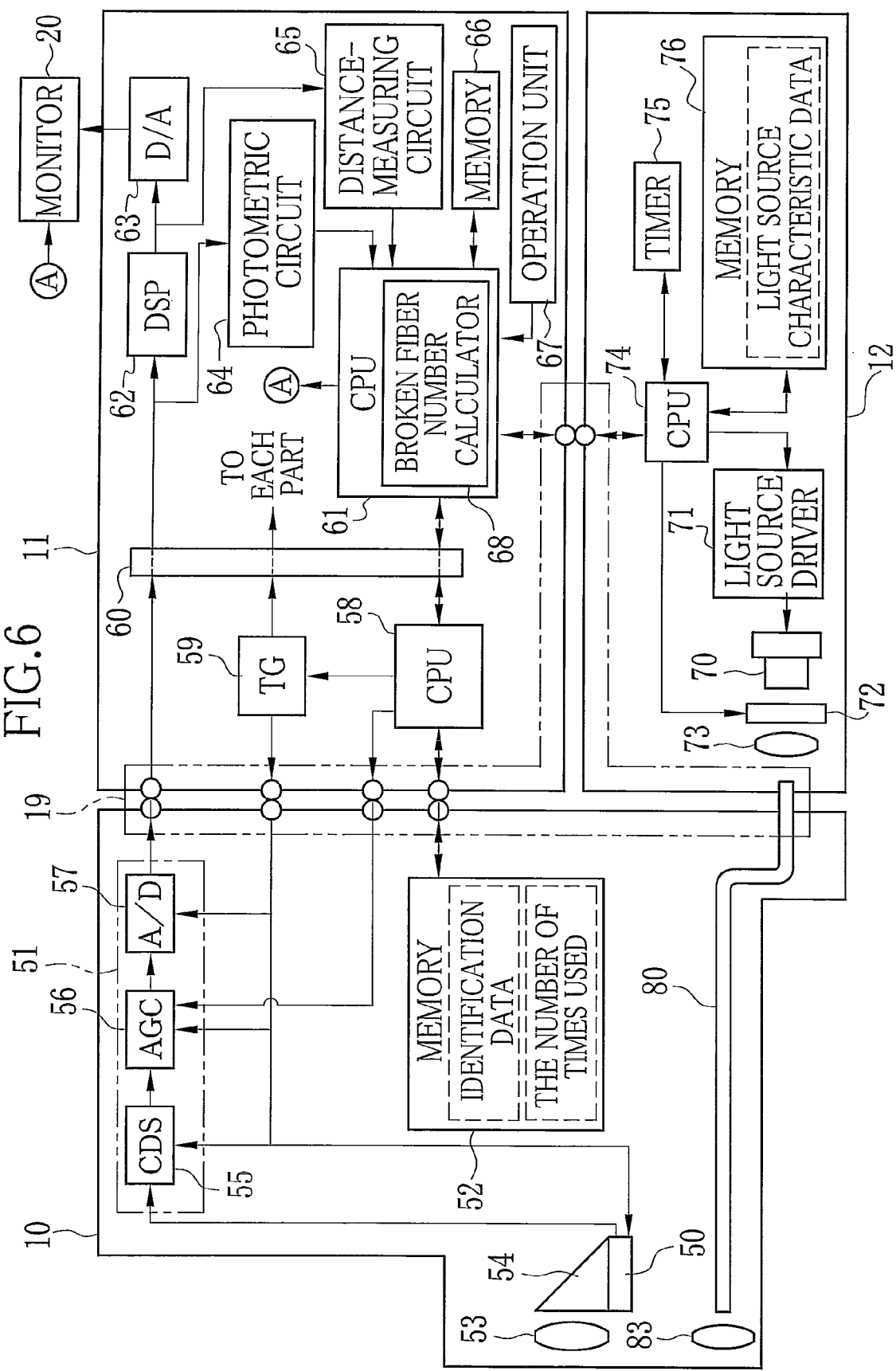
FIG. 6 is a block diagram showing the configuration of an endoscope system.

Referring to FIG. 6, the electronic endoscope 10 has the solid-state image sensor 50 disposed in the distal portion 16, and an analog front end processor (AFE) 51 and a memory 52 disposed in the operation section 14. The solid-state image sensor 50 such as a CCD image sensor is so disposed that object light passing through the objective lens system 53 and the prism 54 is incident upon its light receiving surface. The light receiving surface is equipped with a color filter having a plurality of color segments (for example, primary-colors filter of Bayer arrangement).

The AFE 51 is constituted of a correlated double sampling circuit (CDS) 55, an automatic gain controller (AGC) 56 being an amplifier and an analog-to-digital converter (A/D) 57. The CDS 55 applies correlated double sampling processing to the image signal from the solid-state image sensor 50 in order to remove reset noise and amplifier noise. The AGC 56 amplifies the image signal without noise by gain that the processor device 11 has designated. The A/D 57 converts the amplified image signal into a digital signal of a predetermined bit number, and inputs it to the processor device 11 through the connector 19.

The memory 52 is a nonvolatile memory such as a flash memory. The memory 52 stores identification data for identifying the model of the electronic endoscope 10 and the number of times the electronic endoscope 10 has been used. No sooner is the electronic endoscope 10 connected to the processor device 11, than the processor device 11 reads out the identification data and the number of times the electronic endoscope 10 has been used.

The processor device 11 includes a CPU 58, a timing generator (TG) 59, an isolation device (ID) 60, another CPU 61, a digital signal processor (DSP) 62, a digital-to-analog converter (D/A) 63, a photometric circuit 64, a distance-measuring circuit 65, a memory 66 and an operation unit 67. The CPU 48 controls actuation of the electronic endoscope 10. The TG 49 generates various timing pulses. The ID 60 electrically separates the electronic endoscope 10 from the processor device 11. The CPU 61 controls actuation of the processor device 11. The DSP 62 applies image processing to the digital signal to produce image data. The D/A 63 converts the image data produced by the DSP 62 into an analog signal, and outputs it to the monitor 20. The photometric circuit 64 calculates luminance of light supplied through the light guide 80 in the light guide inspection mode. The distance-measuring circuit 65 calculates the distance "L" from the test chart 43 to the front face 16a of the distal portion 16 in that mode. The memory 66 stores a table that lists the total number of the optical fibers 81 contained in the light guide 80 on a model of electronic endoscope 10 basis. The operation unit 67 inputs a control signal to the CPU 61 in response to actuation of a user. The CPU 61 is provided with a broken fiber number calculator 68 that calculates the number of broken optical fibers 81 in the light guide 80.

Upon connecting the electronic endoscope 10 to the processor device 11, the CPU 58 reads the identification data and the number of times the electronic endoscope 10 has been used out of the memory 52, and inputs them to the CPU 61 via the ID 60. The CPU 58 also increments the number which is read out of the memory 52 by "1", and rewrites a new number into the memory 52. The identification data is used in the light guide inspection mode. The number of times the electronic endoscope 10 has been used is available for the purpose of reminding a user of execution of a light guide inspection. In this embodiment, the CPU 58 functions as a count detector.

The CPU 58 drives the TG 59 on the basis of an operation start command from the CPU 61. The TG 49 generates drive pulses (a vertical/horizontal scanning pulse, a reset pulse and the like) for the solid-state image sensor 50 and a synchronization pulse for the AFE 51, and inputs them into the electronic endoscope 10 through the connector 19. The solid-state image sensor 50 captures an image in response to the drive pulses from the TG 59, and outputs an image signal. The CPU 58 also adjusts gain of the AGC 56. In this embodiment, the CPU 58 functions as a gain adjuster.

The TG 59 also supplies the DSP 62, the CPU 61 and the like through the ID 60 with a synchronization pulse for signal processing. The ID 60 is an isolator made of a photocoupler and the like. The image signal is inputted from the AFE 51 to the DSP 62 through the ID 60.

The DSP 62 subjects the inputted image signal to color separation, color interpolation, gain correction, white balance correction, gamma correction and the like to produce image data.

The photometric circuit 64 and the distance-measuring circuit 65 operate in the light guide inspection mode. When the operation unit 67 is operated with the cap 40 attached to the distal portion 16 of the electronic endoscope 10, the electronic endoscope 10 is set into the light guide inspection mode. The light transmitted through the light guide 80 illuminates the test chart 43. During illumination, the solid-state image sensor 50 captures an image of the test chart 43 to output an image signal. The photometric circuit 64 receives the image signal of a single frame from the AFE 51, and adds up a luminance value of every pixel in an effective area. Then, the AFE 51 divides a total luminance value by a total pixel number to obtain an average luminance value "Y". The distance-measuring circuit 65 detects an area corresponding to the distance-measuring area 43a of the test chart 43 from the image data produced by the DSP 62, and calculates the distance "L" from the test chart 43 to the front face 16a of the distal portion 16 on the basis of the size of the detected area. The distance-measuring circuit 65 has a function expressing the relation between the size of the distance-measuring area 43a and the distance "L", and hence obtains the distance "L" by proportional calculation.

The broken fiber number calculator 68, which operates in the light guide test mode, calculates the number "N" of broken optical fibers out of the optical fibers 81 in accordance with the following expression (1):

$$N = M \times (1 - Y/I(R,L)) \tag{1}$$

Wherein, "M" represents the total number of the optical fibers 81. "Y" represents the average luminance value, and "I(R,L)" represents an ideal average luminance value.

The total number "M" of the optical fibers 81 is read out of the memory 66 in accordance with the identification data the CPU 58 has read. The average luminance value "Y" is detected by the photometric circuit 64, as described above. The ideal average luminance value "I(R,L)" is an estimated average luminance value of the test chart 43 on the assumption that there are no broken optical fibers 81 in the light guide 80 (non defect state). The ideal average luminance value "I(R,L)" is a function of a damping rate "R" in the amount of light emitted from a light source 70 and the distance "L". The distance "L" is an adjustment parameter for adjusting a detection error due to attachment misalignment between the cap 40 and the distal portion 16.

When the endoscope system 2 is set into the light guide inspection mode, the CPU 61 displays the detected number "N" on the monitor 20. At the same time, the CPU 61 issues a command to the CPU 58, and adjusts the gain of the AGC 56 so as to eliminate a decrease "D (=I(R,L)−Y)" in the average luminance value that is caused by a shortage of light due to the broken optical fibers 81, in other words, to be D=0. Also, the CPU 61 displays a warning message for urging the user to replace the electronic endoscope 10 on the monitor 20, when the number "N" is a predetermined number "$N_0$" (for example, a half of the total number "M") or more.

In addition, the CPU 61 displays a message for reminding the user of the inspection of the light guide 80 whenever the number of times the electronic endoscope 10 was used, which the CPU 58 has read out of the memory 52, coincides with predetermined numbers (for example, 100, 200, 300 . . . ). In this embodiment, the CPU 61 and the monitor 20 function as first to third notification sections.

The light source device 12 is constituted of a light source 70 such as a xenon lamp and a halogen lamp, a light source driver 71 for driving the light source 70, an aperture stop mechanism 72 and a condenser lens 73 disposed between the light source 70 and the light guide 80, a CPU 74 for controlling the light source driver 71 and the aperture stop mechanism 72 by communicating with the CPU 61 of the processor device 11, a timer 75 for counting the used time of the light source 70 and a memory 76 for storing light source property data. The aperture stop mechanism 72 increases or decreases the amount of light incident upon the light guide 80. The condense lens 73 condenses light passing through the aperture stop mechanism 72, and leads it into an entry of the light guide 80.

Figure 7:
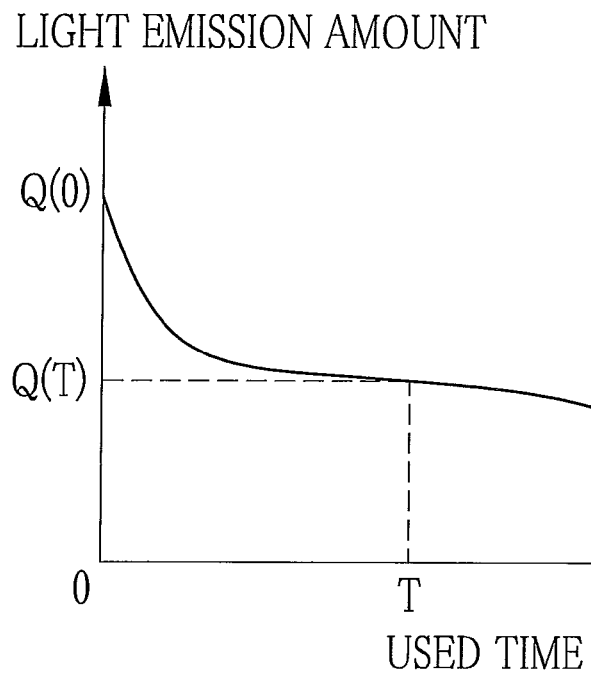
FIG. 7 is a graph showing an example of light source property data.

The memory 76 stores the light source property data as shown in FIG. 7. The light source property data shows the relation between a light emission amount and the used time in driving the light source 70 under a fixed condition. As is apparent in FIG. 7, the light emission amount of the light source 70 is damped with increase in the used time. The CPU 74 obtains the light emission amount "Q(T)" of the light source 70 at used time "T" counted by the timer 75, and calculates a light damping rate "R (=1−Q(T)/Q(0))".

Figure 8:
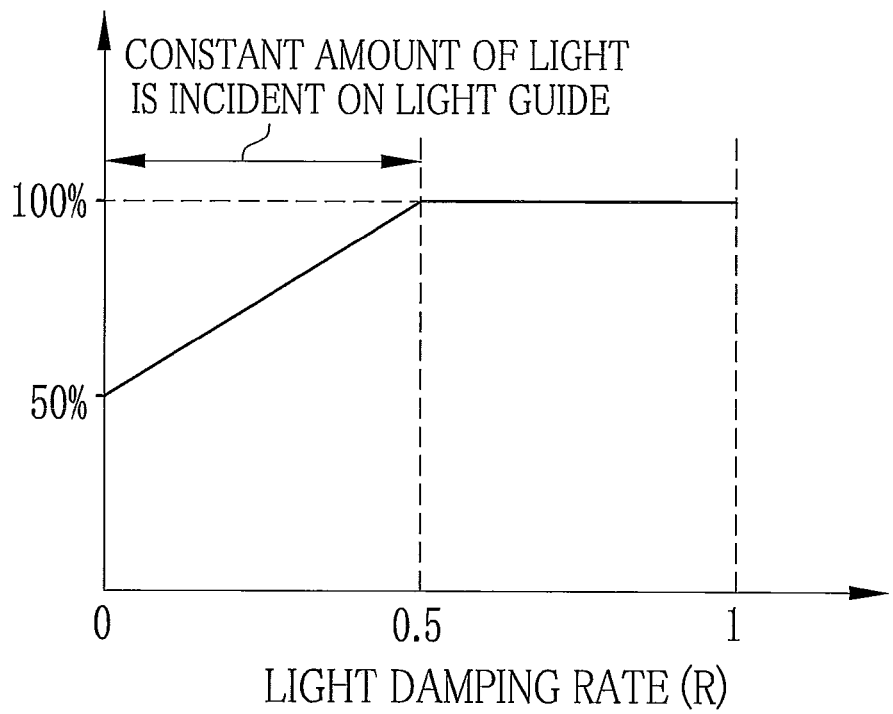
FIG. 8 is a graph showing setting of opening with respect to a light damping rate.

The CPU 74, as shown in FIG. 8, sets opening of the aperture stop mechanism 72 in accordance with the light damping rate "R". In other words, the opening is proportional to the light damping rate "R" within the confines of $0 \leq R \leq 0.5$, in such a manner that the opening is 50% at R=0 (t=0) and becomes 100% at R=0.5. On the other hand, the opening is fixed at 100% within the confines of $0.5 \leq R \leq 1$. By setting the opening like this, the amount of light incident on the light guide 80 is kept constant at an initial value (a half of an initial light emission amount "Q(0)") within the confines of $0 \leq R \leq 0.5$, and decreases from the initial value within the confines of $0.5 < R \leq 1$.

Accordingly, the amount of light exiting from the lighting windows 31 is constant within the confines of $0 \leq R \leq 0.5$ irrespective of the light damping rate "R", and decreases within the confines of $0.5 < R \leq 1$ with increase in the light damping rate "R". Thus, the following expressions (2a) and (2b) represent the ideal average luminance value "I(R,L)" with the use of the light damping rate "R" and the distance "L" as adjustment parameters.

In the case of $0 \leq R \leq 0.5$:

$$I(R,L) = I_0 \times (L_0/L)^2 \quad (2a)$$

In the case of $0.5 < R \leq 1$:

$$I(R,L) = 2 \times (1-R) \times I_0 \times (L_0/L)^2 \quad (2b)$$

Wherein, "$I_0$" represents an ideal average luminance value of the test chart 43 at R=0 and L=$L_0$. The ideal average luminance value "$I_0$" and an ideal distance "$L_0$" have been stored on the memory 66 in advance. The broken fiber number calculator 68 reads the values from the memory 66, and calculates the number "N" of broken optical fibers 81 by using the above expressions (1), (2a) and (2b).

Figure 9:
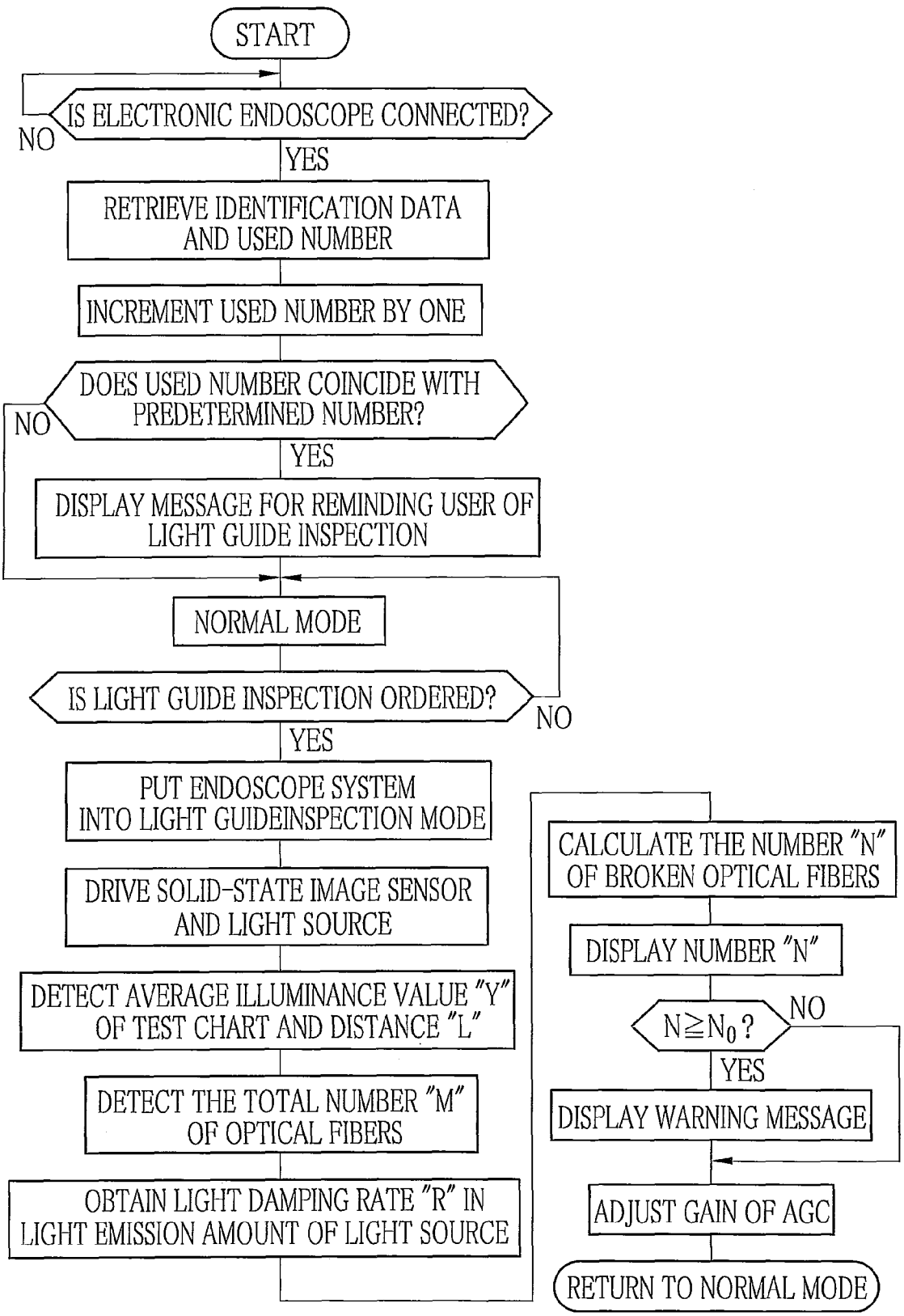
FIG. 9 is a flowchart showing the operation of the endoscope system.

Next, the operation of the endoscope system 2 having aforementioned structure will be described along a flowchart of FIG. 9. The CPU 58 of the processor device 11 first detects whether or not the electronic endoscope 10 is connected to the processor device 11. If YES, the CPU reads the identification data and the number of times the electronic endoscope 10 has been used out of the memory 52 of the electronic endoscope 10, and rewrites a new number on the memory 52 by incrementing the read number by "1".

Then, the CPU 61 judges whether or not the number of times the electronic endoscope 10 has been used, which is read by the CPU 58, coincides with any of the predetermined numbers (for example, 100, 200, 300 . . . ). When the number coincides with the predetermined number, the message reminding the user of the light guide inspection is displayed on the monitor 20 (which says, for example, "This endoscope has been used a hundred times. Please execute light guide inspection.") When the number does not coincide with the predetermined number, on the other hand, the endoscope system 2 is shifted into a normal mode for capturing the image of the inside body site.

During the normal mode, when the user attaches the cap 40 to the distal portion of the electronic endoscope 10 and orders the light guide inspection from the operation unit 67, the CPU 61 starts to inspect the light guide 80. In the light guide inspection mode, firstly, the CPU 58 drives the solid-state image sensor 50, and the CPU 74 drives the light source 70. Thus, the solid-state image sensor 50 captures the image of the test chart 43, while the light exiting from the light guide 80 is applied on the test chart 43.

Since the image signal outputted from the solid-state image sensor 50 is inputted to the processor device 11 through the AFE 51, the photometric circuit 64 detects the average luminance value "Y" of the test chart 43. Also, the DSP 62 converts the image signal into the image data, and the distance-measuring circuit 65 detects the distance "L" from the test chart 43 to the front face 16a of the distal portion 16.

Then, the CPU 61 retrieves the total number "M" of the optical fibers 81 contained in the light guide 80 on the basis of the model of the electronic endoscope 10 read by the CPU 58. Based on the used time of the light source 70 read out of the light source device 12, the CPU 61 obtains the light damping rate "R" in the light emission amount of the light source 70 at that point in time. The CPU 74 successively sets the opening of the aperture stop mechanism 72 based on the obtained light damping rate "R".

The broken fiber number calculator 68 calculates the number "N" of broken optical fibers 81 on the basis of the aforementioned expressions (1), (2a) and (2b) with the use of the detected average luminance value "Y" and distance "L" of the test chart 43, the total number "M" of the optical fibers 81 and the light damping rate "R" in the light emission amount.

The CPU 61 displays the number "N" of broken optical fibers 81 calculated by the broken fiber number calculator 68 on the monitor 20. When the number "N" reaches or exceeds the predetermined number "$N_0$" (for example, a half of the total number "M"), the CPU 61 displays the warning message on the monitor 20 (which says, for example, "warning: light guide has deteriorated. Please replace endoscope.").

The CPU 58, on the other hand, adjusts the gain of the AGC 56 so as to eliminate the decrease "D (=I(R,L)−Y)" in the average luminance value due to a broke of the optical fibers 81, and returns to the normal mode.

As described above, the endoscope system 2 has the light guide inspection mode for inspecting the light guide 80 of the electronic endoscope 10. When the endoscope system 2 is put into the light guide inspection mode in such a state that the cap 40 with the test chart 43 is attached to the distal portion 16 of the electronic endoscope 10, the number of broken optical fibers 81 is detected. The user can correctly grasp the number of the broken optical fibers 81 anytime, and hence replace the electronic endoscope 10 at appropriate timing. Gain adjustment by the AGC 56 corrects a shortage of luminance value due to a break of the optical fibers 81. Therefore, it is possible to alleviate decrease in luminance of the image of the human body cavity.

The endoscope system 2 also detects the number of times the electronic endoscope 10 has been used. Whenever the number reaches to any of the predetermined numbers, the endoscope system 2 reminds the user of the inspection of the light guide 80. Thus, the user can carry out the inspection at appropriate timing without managing an inspection schedule.

Figure 10:
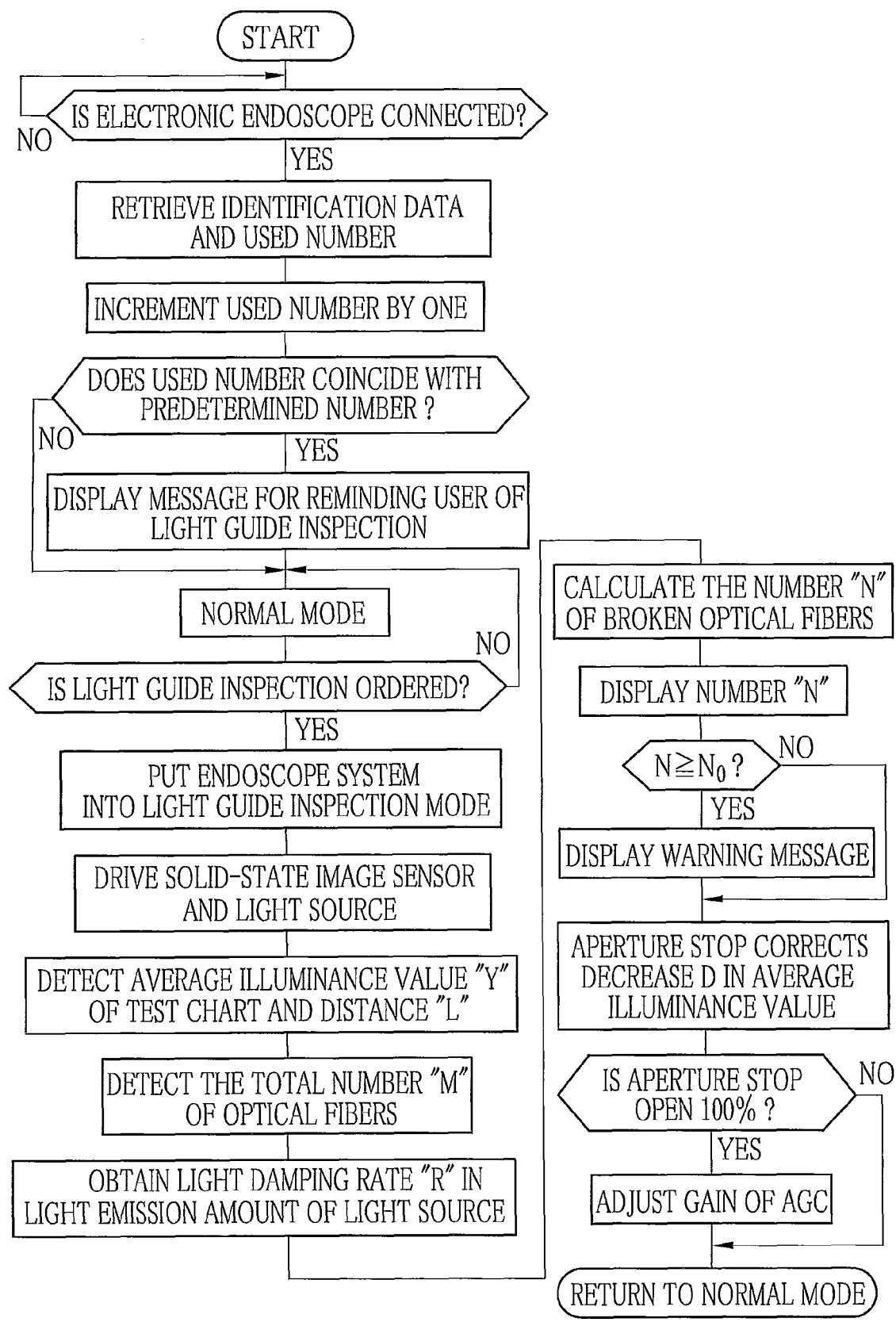
FIG. 10 is a flowchart showing the operation of an endoscope system according to another embodiment.

In the foregoing embodiment, gain adjustment by the AGC 56 corrects the decrease "D" in the average luminance value due to a break of the optical fibers 81. Instead of this, as shown in FIG. 10, adjustment in the opening of the aperture stop mechanism 72 (that is, adjustment in the amount of light incident on the light guide 80) may correct the decrease "D" in the average luminance value, after calculating and displaying the number "N" of broken optical fibers 81. After the aperture stop mechanism 72 has already been open 100% to its maximum and the amount of incident light cannot be increased anymore, the AGC 56 adjusts (increases) the gain.

In the foregoing embodiments, the amount of light emitted from the light source 70 decreases with the lapse of time. The present invention, however, may use another light source such as a LED whose light emission amount does not damp with time. In this case, the ideal average luminance value "I(R,L)" is independent of the light damping rate "R".

In the foregoing embodiments, the distance-measuring area 43a of the test chart 43 is the circular black area. However, the shape and color of the distance-measuring area 43a is appropriately changeable. Also, using a mechanism that always makes the distance "L" constant in attaching the cap 40 to the top section 16 of the electronic endoscope 10 eliminates the need for the distance-measuring area 43a. In this case, the ideal average luminance value "I(R,L)" is independent of the distance "L". The distance-measuring area 43a, however, may be used for a purpose except for distance measurement, so that it is preferable that the test chart 43 has the distance-measuring area 43a even if the distance "L" is always constant. For example, the distance-measuring area 43a is available to detect whether or not the cap 40 is attached to the distal portion 16 of the electronic endoscope 10. If the distance-measuring circuit 65 does not detect the distance-measuring area 43a, the light guide test mode is suspended to prevent an error in the inspection.

In the foregoing embodiments, the photometric area 43b of the test chart 43 is in another color such as 25% gray, instead of 18% gray.

In the foregoing embodiments, the message reminding the user of the inspection, the message saying the detected number "N" of the broken fibers and the warning message saying that the number "N" reaches or exceeds the predetermined number are displayed on the monitor 20. However, the endoscope system 2 may notify the user of the messages by another way such as voice.

The cap 40 may be connected to the processor device 11 or the light source device 12 with a string or the like. Moreover, a cap may be integrally provided in the processor device 11 or the light source device 12.

In the foregoing embodiment, the photometric circuit 64 calculates the average luminance value "Y" on the basis of the image signal inputted from the AFE 51. In the present invention, the photometric circuit 64 may calculate the average luminance value "Y" on the basis of the image data generated by the DSP 62. In this case, the DSP 62 generates the image data by applying the gamma correction on the image signal, so that the relation between a luminance value and a light amount is nonlinear. Thus, in this case, the distance-measuring area 43b of the test chart 43 is preferably in a gray scale of approximately 18% gray which roughly maintains the relation between the luminance value and the light amount linear.

In the foregoing embodiments, the CPU 74 of the light source device 12 sets an initial opening value at 50% in the case of the light damping rate R=0, but the initial opening value is appropriately changeable.

In the foregoing embodiment, the solid-state image sensor 50 is disposed in the distal portion 16 of the electronic endoscope 10. The solid-state image sensor 50 may be disposed in any section in the electronic endoscope 10 such as the operation section 14. When the solid-state image sensor 50 is disposed in the operation section 14, an optical system such as an optical fiber may extend in the insert section so that object light incident from the image capturing window 30 of the distal portion 16 forms an image on the light receiving surface of the solid-state image sensor 50.

In the present invention, the processor device 11 and the light source device 12 may be integrated into a single case.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system including an electronic endoscope with a solid-state image sensor, a processor device for producing an image from an image signal from said solid-state image sensor and a light source device, said electronic endoscope including a light guide for transmitting light which illuminates an object when said solid-state image sensor captures said image of said object, said light guide having a bundle of optical fibers, said endoscope system comprising:

a cap having a test chart, said cap being attached to a distal portion of said electronic endoscope so that said solid-state image sensor captures an image of said test chart to output a chart image signal;

a photometric circuit for measuring an average luminance value of said test chart from said chart image signal; and a broken fiber number calculator for calculating the number "N" of broken optical fibers of said optical fibers that satisfies the following expression:

$$N = M \times (1 - Y/I)$$

wherein, "Y" represents said average luminance value detected by said photometric circuit, "I" represents an ideal average luminance value when all of said optical fibers are conducting, and "M" represents the total number of said optical fibers.

2. The endoscope system as recited in claim 1, wherein said processor device contains said photometric circuit and said broken fiber number calculator.

3. The endoscope system as recited in claim 2, wherein said processor device further comprises:
   a first notification section for notifying a user of said number of said broken optical fibers.

4. The endoscope system as recited in claim 2, wherein said processor device further comprises:
   a second notification section for issuing a warning message, when said number of said broken optical fibers reaches or exceeds a predetermined number.

5. The endoscope system as recited in claim 2, wherein said processor device further comprises:
   an operation unit for causing said endoscope system to set into a light guide inspection mode, said number of said broken optical fibers being calculated in said light guide inspection mode;
   a count detector for detecting the number of times said electronic endoscope has been used; and
   a third notification section for issuing a message that reminds a user of inspection of said light guide, when said number detected by said count detector coincides with a predetermined number.

6. The endoscope system as recited in claim 2, wherein said electronic endoscope further comprises:
   an amplifier for amplifying said chart image signal; and
   a gain adjuster for adjusting gain of said amplifier to correct decrease in said average luminance value with respect to said ideal average luminance value.

7. The endoscope system as recited in claim 2, wherein said test chart has a photometric area of 18% gray, and said photometric circuit calculates said average luminance value of said test chart from luminance of said photometric area from said chart image signal.

8. The endoscope system as recited in claim 2, wherein said light source device comprises:
   a light source for emitting said light;
   an aperture stop mechanism disposed between said light source and said light guide for leading said light into said light guide;
   a timer for counting used time of said light source;
   a memory for storing light source property data which indicates the relation between a light emission amount and said used time of said light source; and
   an aperture stop controller which retrieves a light damping rate in said light emission amount from said used time and said light source property data, and controls opening of said aperture stop mechanism so that the amount of said light led into said light guide is made constant irrespective of said light damping rate.

9. The endoscope system as recited in claim 8, wherein when said light damping rate is larger than a predetermined value and said amount of said light led into said light guide is less than a predetermined value though said aperture stop mechanism is open to its maximum, said ideal average luminance value is corrected based on said light damping rate.

10. The endoscope system as recited in claim 2, wherein said test chart is provided with a distance-measuring area, said processor device further comprises:
    a distance-measuring circuit for detecting distance from said distal portion to said test chart on the basis of the size of said distance-measuring area from said chart image signal, and said ideal average luminance value is corrected based on said distance detected by said distance-measuring circuit.

11. The endoscope system as recited in claim 10, wherein said distance-measuring area is a circular black area.

12. A method for inspecting an electronic endoscope including a solid-state image sensor and a light guide constructed by a bundle of optical fibers, said method comprising the steps of:
    attaching a cap with a test chart to a distal portion of said electronic endoscope;
    illuminating said test chart with light which is emitted from a light source and transmitted through said light guide;
    capturing an image of said test chart by said solid-state image sensor;
    detecting an average luminance value of said light from a chart image signal outputted from said solid-state image sensor;
    calculating the number "N" of broken optical fibers of said optical fibers that satisfies the following expression:

$$N = M \times (1 - Y/I)$$

wherein, "Y" represents said detected average luminance value, "I" represents an ideal average luminance value when all of said optical fibers are conducting, and "M" represents the total number of said optical fibers.

* * * * *